United States Patent
Eyerich et al.

(10) Patent No.: US 12,031,182 B2
(45) Date of Patent: Jul. 9, 2024

(54) DIFFERENTIAL DIAGNOSIS OF ECZEMA AND PSORIASIS

(71) Applicants: HELMHOLTZ ZENTRUM MÜNCHEN—DEUTSCHES FORSCHUNGSZENTRUM FÜR GESUNDHEIT UND UMWELT (GMBH), Neuherberg (DE); KLINIKUM RECHTS DER ISAR DER TECHNISCHEN UNIVERSITÄT MÜNCHEN, Munich (DE)

(72) Inventors: Kilian Eyerich, Munich (DE); Carsten Schmidt-Weber, Munich (DE); Bettina Knapp, Prien a. Chiemsee (DE)

(73) Assignees: HELMHOLTZ ZENTRUM MÜNCHEN— DEUTSCHES FORSCHUNGSZENTRUM FÜR GESUNDHEIT UND UMWELT (GMBH), Neuherberg (DE); KLINIKUM RECHTS DER ISAR DER TECHNISCHEN UNIVERSITÄT MÜNCHEN, Munich (DE)

( * ) Notice: Subject to any disclaimer, the term of this patent is extended or adjusted under 35 U.S.C. 154(b) by 1118 days.

(21) Appl. No.: 16/428,411

(22) Filed: May 31, 2019

(65) Prior Publication Data
US 2019/0316201 A1 Oct. 17, 2019

Related U.S. Application Data

(62) Division of application No. 15/304,364, filed as application No. PCT/EP2015/058149 on Apr. 15, 2015, now abandoned.

(30) Foreign Application Priority Data

Apr. 15, 2014 (EP) .................................. 14164807

(51) Int. Cl.
| | |
|---|---|
| C12Q 1/6883 | (2018.01) |
| C07K 16/18 | (2006.01) |
| C07K 16/22 | (2006.01) |
| C07K 16/24 | (2006.01) |
| C07K 16/28 | (2006.01) |
| C07K 16/40 | (2006.01) |
| G01N 33/68 | (2006.01) |

(52) U.S. Cl.
CPC ............ *C12Q 1/6883* (2013.01); *C07K 16/24* (2013.01); *C07K 16/40* (2013.01); *G01N 33/6881* (2013.01); *C07K 16/18* (2013.01); *C07K 16/22* (2013.01); *C07K 16/244* (2013.01); *C07K 16/2866* (2013.01); *C12Q 2600/112* (2013.01); *C12Q 2600/158* (2013.01); *C12Q 2600/16* (2013.01); *G01N 2800/205* (2013.01)

(58) Field of Classification Search
None
See application file for complete search history.

(56) References Cited

U.S. PATENT DOCUMENTS 4,591,570 A * 5/1986 Chang ................. G01N 33/552
436/815

FOREIGN PATENT DOCUMENTS

| EP | 0239400 A2 | 9/1987 |
|---|---|---|
| WO | 89/09622 A1 | 10/1989 |
| WO | 90/07861 A1 | 7/1990 |
| WO | 91/10741 A1 | 7/1991 |
| WO | 94/02602 A1 | 2/1994 |
| WO | 96/33735 A1 | 10/1996 |
| WO | 96/34096 A1 | 10/1996 |

OTHER PUBLICATIONS

Agilent SurePrint G3 Human Gene Expression 8x60K Microarray (G4851A) Application Note (Published on Mar. 30, 2012).*
Quaranta et al. 'Intraindividual genome expression analysis reveals a specific molecular signature of psoriasis and eczema.' Science Translational Medicine 6(244) pp. 1-10 2014. p. 244ra90 DOI: 10.1126/scitranslmed.3008946.*
Backmann et al. 'A label-free immunosensor array using single-chainantibody fragments.' PNAS 102(41):14587-14592, 2005.*
Christopher M. Bishop, et al.; "Pattern Recognition and Machine Learning"; Springer Science+Business Media, LLC; (2006); Abstract Only.
Joseph Sambrook, et al.; "Molecular Cloning, A Laboratory Manual"; Third Edition; vol. 2; Cold Spring Harbor Laboratory Press; (2001); Abstract Only.
Ed Harlow, et al.; "Antibodies, A Laboratory Manual"; Cold Spring Harbor Laboratory Press; (1988); Abstract Only.
Budczies, J. et al. Cutoff Finder: A Comprehensive and Straightforward Web Application Enabling Rapid Biomaker Cutoff Optimization. PLoS One, 1-7(2012).

(Continued)

*Primary Examiner* — Nora M Rooney
(74) *Attorney, Agent, or Firm* — GREENBLUM & BERNSTEIN, P.L.C.

(57) ABSTRACT

The present invention relates to a method of diagnosing eczema and/or psoriasis, wherein said method differentiates between eczema and psoriasis, and comprises determining the expression of at least two markers in a sample taken from an individual, wherein said at least two markers are selected from CCL27, NOS2, IL36G, KLK13, SOST, NPTX1, PLA2G4D, GDA, IL36A, TGM1, CLEC4G, IL13, TCN1, TMPRSS11D and RHCG, provided that said at least two markers consist of or comprise (a) CCL27 and NOS2; (b) CCL27 and KLK13; (c) IL36G and KLK13; (d) CCL27 and IL36G; (e) NOS2 and IL36G; (f) NOS2 and KLK13; (g) SOST; or (h) NPTX1; and assessing on the basis of the expression of said at least two markers whether the individual is afflicted with eczema and/or psoriasis.

20 Claims, 3 Drawing Sheets

Figure 1:
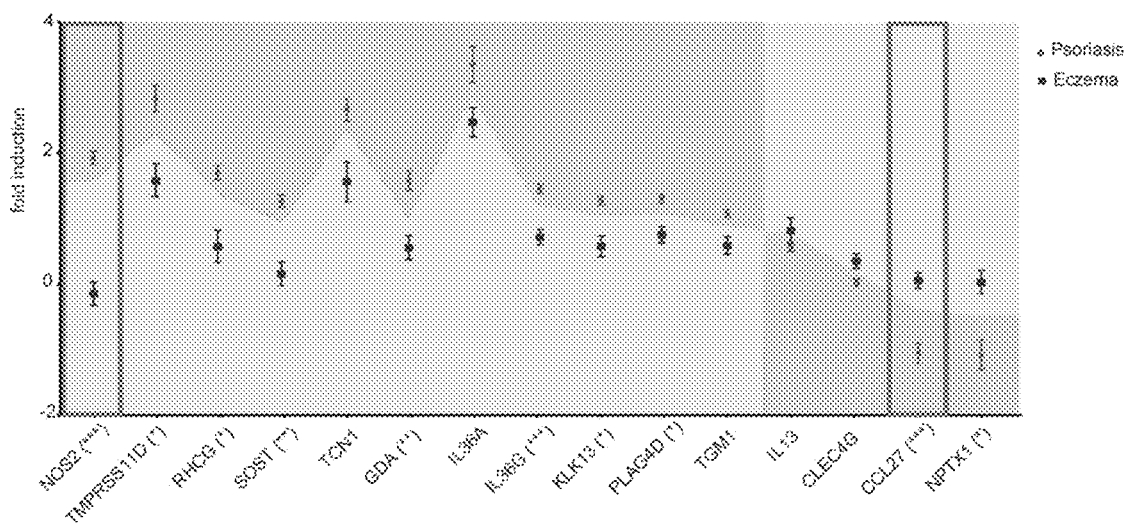
Figure 1:
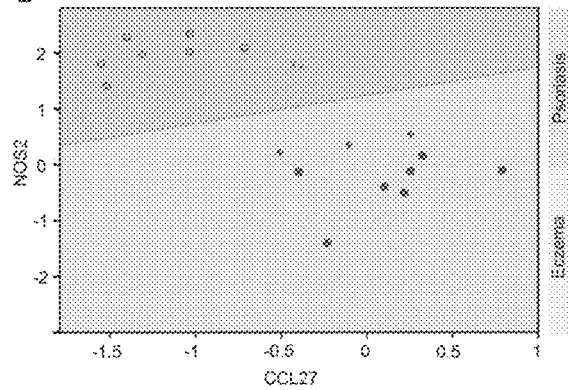
Figure 1:
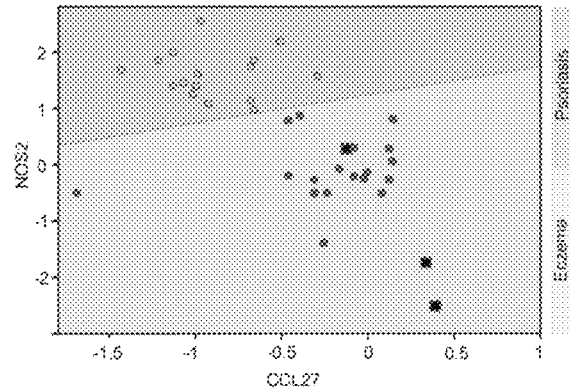
Figure 1:
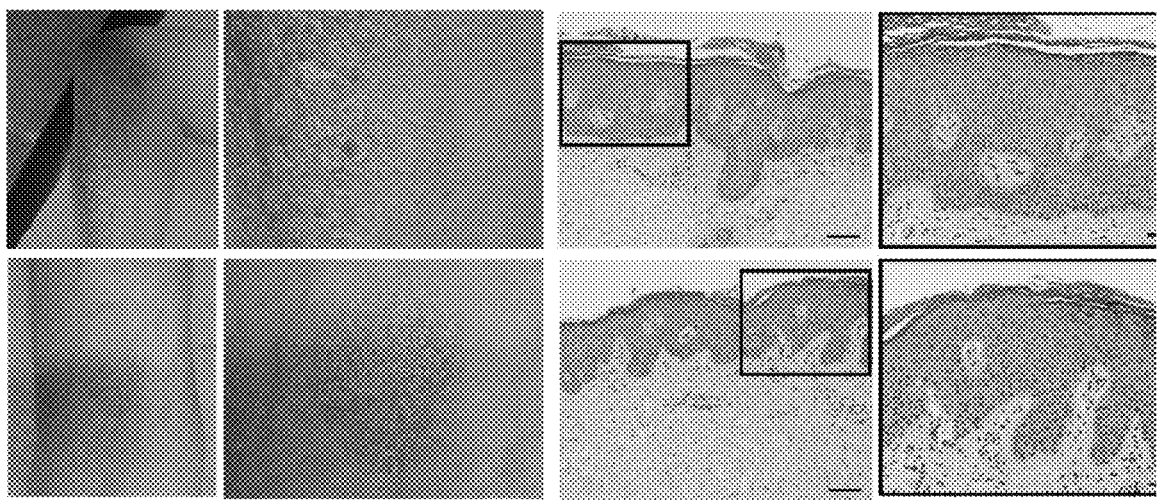

Specification includes a Sequence Listing.

(56) References Cited

OTHER PUBLICATIONS

Ainali, C. et. al Transcriptome classification reveals molecular subtypes in psoriasis. BMC Genomics 13, 472: 1-15 (2012).
Guo, P. et al. Gene expression profile based classification models of psoriasis. Genomics 103, 48-55 (2014).
Sajda, P. Machine learning for detection and diagnosis of disease. Annual Review of Biomedical Engineering 8, 537-565 (2006).
International Search Report and Written Opinion of related International Application No. PCT/EP2015/058149 dated Jul. 1, 2015.
Human Genome U95 Set, AFFYMETRIX; 1 page. http://www attymetrix.com/products/arrays/specitic/hgu95.com.
GeneChip Human Genome U133 Set; Gene Expression Monitoring, AFFYMETRIX; Feb. 2003; pp. 1-2_http://www.affymetrix.com/support/technical/datasheets/hgu133_datasheet.pdf.
Constantine et al.; "Use of GeneChip high-density oligonucleotide arrays for gene expression monitoring"; Innovations Forum; Affymetrix, Inc; Jan. 1998; pp. 11-14; Santa Clara, CA.
Nomura et al.; "Distinct patterns of gene expression in the skin lesions of atopic dermatitis and psoriasis: A gene microarray analysis"; Journal of Allergy and Clinical Immunology; Dec. 1, 2003; pp. 1195-1202; vol. 112; No. 6.
M. Kamsteeg et al.; "Molecular diagnostics of psoriasis, atopic dermatitis, allergic contact dermatitis and irritant contact dermatitis"; British Journal of Dermatology; Clinical and Laboratory Investigations; Mar. 1, 2010; pp. 568-578; vol. 162; Netherlands.
Mayte Suarez-Farinas et al.; "Expanding the Psoriasis Disease Profile: Interrogation of the Skin and Serum of Patients with Moderate-to-Sereve Psoriasis"; Journal of Investigative Dermatology; Jul. 5, 2012; pp. 2552-2564; vol. 132; No. 11.
S.M. Banu et al.; "A Mobile/Desktop Medical Application for Automatic Differential Diagnosis of Psoriasis Lesions"; 2013 Second International Conference On E-Learning and E-Technologies in Education ICEEE); Sep. 13, 2013; pp. 186-191.
L.C. Zaba et al.; "Identification of TNF-related apoptosis-inducing ligand and other molecules that distinguish inflammatory from resident dendritic cells in patients with psoriasis", J Allergy Clin Immunol, 2010, vol. 125, No. 5, pp. 1261-1268.
T. Bieber, "Atopic Dermatitis"; Mechanisms of Disease; The New England Journal of Medicine; 2008; pp. 1483-1494; vol. 358.
F.O. Nestle et. al.; "Psoriasis"; Mechanisms of Disease; The New England Journal of Medicine; 2009; pp. 496-509; vol. 361.
K. Eyerich et al.; "Immunology of atopic exzema: Overcoming the Th1/Th2 paradigm"; Allergy; European Journal of Allergy and Clinical Immunology; 2013; pp. 974-982; vol. 68.
E. Guttman-Yassky et al.; "Contrasting pathogenesis of atopic dermatitis and psoriasis—Part II: Immune cell subsets and therapeutic concepts"; Journal of Clinical Immunology; Nov. 6, 2011; pp. 1420-1428; vol. 127.
S. Eyerich et al.; "Mutual Antagonism of T Cells Causing Psoriasis and Atopic Eczema"; The New England Journal of Medicine; 2011; pp. 29-36; vol. 365.
K. Ghoreshi et al.; "Interleukin-4 therapy of psoriasis induces Th2 responses and improves human autoimmune disease"; Nature Medicine; 2003; pp. 40-46; vol. 9; No. 1.
M. Suarez-Farinas et aL; "Nonlesional atopic dermatitis skin is characterized by broad terminal differentiation defects and variable immune abnormalities"; Journal of Allegy Clinical Immunology; 2011; pp. 954-964; vol. 127.
S. Tian et aL; "Meta-Analysis Derived {MAD} Transcriptome of PsoriasisDefines the "Core" Pathoigenesis of Disease"; PLOS One; Sep. 2012; pp. 1-15; vol. 7; Issue 9; e44274.
J. Wenzel et al.; "Gene Expression Profiling of Lichen Planus Reflects CXCL9+-Mediated Inflammation and Distinguishes this Disease from Atopic Dermatitis and Psoriasis"; Journal of Investigative Dermatology; 2008; pp. 67-78; vol. 128.
G.J. de Jongh et aL; "High Expression Levels of Keratinocyte Antimicrobial Proteins in Psoriasis Compared with Atopic Dermatitis"; Journal of Investigative Dermatology; 2005; pp. 1163-1173; vol. 125.
E. Guttman-Yassky et al.; "Broad defects in epidermal cornification in atopic dermatitis identified through genomic analysis"; Journal of Allergy Clinical Immunology; 2009; pp. 1235-1244; vol. 124.
G. Kohler et aL; "Continuous cultures of fused cells secreting antibody of predefined specificity"; Nature; Aug. 7, 1975; pp. 495-497; vol. 256.
G. Galfre et al.; "[1] Preparation of Monoclonal Antibodies: Strategies and Procedures"; Methods in Enzymology; 1981, pp. 3-46; vol. 73.
R. Schier et al_.; "Efficient in vitro affinity maturation of phage antibodies using BIAcore guided selections"; Human Antibodies Hybridomas; 1996; pp. 97-105; vol. 7.
Ann-Cristin Malmborg et aL; "BIAcore as a tool in Antibody engineering"; Journal of Immunological Methods; 1995; pp. 7-13; vol. 183.
Intenational Preliminary Report on Patentability (Chapter I) and Written Opinion of the International Searching Authority; PCTIEP2015/058149 dated Oct. 18, 2016.
E Guttman-Yasky et al.; "Major differences in inflammatory dendritic cells and their products distinguish atopic dermatitis from psoriasis", Journal of Allergy and Clinical Immunology; vol. 119; No. 5; Apr. 29, 2007; pp. 1210-1217.

\* cited by examiner

Eczema lesional skin

Psoriasis lesional skin

SEQUENCE LISTING

```
<160> NUMBER OF SEQ ID NOS: 30

<210> SEQ ID NO 1
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Primer for CCL27"
      /organism="Artificial Sequence"

<400> SEQUENCE: 1
aggtcatcca ggtggaactg c                                                 21

<210> SEQ ID NO 2
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Primer for CCL27"
      /organism="Artificial Sequence"

<400> SEQUENCE: 2
tcaaaccact gtgacaggct g                                                 21

<210> SEQ ID NO 3
<211> LENGTH: 20
<212> TYPE: DNA
<213> ORGANISM: Artificial Sequence
<220> FEATURE:
<221> NAME/KEY: source
```

```
<222> LOCATION: 1..20
<223> OTHER INFORMATION: /mol_type="unassigned DNA"
      /note="Primer for NOS2"
      /organism="Artificial Sequence"

<400> SEQUENCE: 3
acacatctgc agacacgtgc                                          20

<210> SEQ ID NO 4
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Primer for NOS2"
      /organism="Artificial Sequence"

<400> SEQUENCE: 4
tcgtgcttgc catcactccg                                          20

<210> SEQ ID NO 5
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Primer for IL36G"
      /organism="Artificial Sequence"

<400> SEQUENCE: 5
catgcaagta tccagaggct c                                        21

<210> SEQ ID NO 6
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Primer for IL36G"
      /organism="Artificial Sequence"

<400> SEQUENCE: 6
ggccatacag atccatgatc                                          20

<210> SEQ ID NO 7
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Primer for KLK13"
      /organism="Artificial Sequence"

<400> SEQUENCE: 7
ctgacaacat gttgtgtgcc                                          20

<210> SEQ ID NO 8
<211> LENGTH: 21
<212> TYPE: DNA
<213> ORGANISM: Artificial Sequence
<220> FEATURE:
```

```
<221> NAME/KEY: source
<222> LOCATION: 1..21
<223> OTHER INFORMATION: /mol_type="unassigned DNA"
      /note="Primer for KLK13"
      /organism="Artificial Sequence"

<400> SEQUENCE: 8
cagtgttctg ttacagacca g                                           21

<210> SEQ ID NO 9
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Primer for SOST"
      /organism="Artificial Sequence"

<400> SEQUENCE: 9
agctggagaa caacaagacc                                             20

<210> SEQ ID NO 10
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Primer for SOST"
      /organism="Artificial Sequence"

<400> SEQUENCE: 10
tcacgtagcg ggtgaagtgc a                                           21

<210> SEQ ID NO 11
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Primer for NPTX1"
      /organism="Artificial Sequence"

<400> SEQUENCE: 11
acgagctggt cctcattgag t                                           21

<210> SEQ ID NO 12
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Primer for NPTX1"
      /organism="Artificial Sequence"

<400> SEQUENCE: 12
gatgtggtgc cacttgccat c                                           21

<210> SEQ ID NO 13
<211> LENGTH: 20
<212> TYPE: DNA
<213> ORGANISM: Artificial Sequence
```

```
<220> FEATURE:
<221> NAME/KEY: source
<222> LOCATION: 1..20
<223> OTHER INFORMATION: /mol_type="unassigned DNA"
      /note="Primer for PLA2G4D"
      /organism="Artificial Sequence"

<400> SEQUENCE: 13
acaccagtca tcctgtgtgg                                                    20

<210> SEQ ID NO 14
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Primer for PLA2G4D"
      /organism="Artificial Sequence"

<400> SEQUENCE: 14
ccgtgactga gtcctcatca                                                    20

<210> SEQ ID NO 15
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Primer for GDA"
      /organism="Artificial Sequence"

<400> SEQUENCE: 15
ccagaacatc gactttgcag a                                                  21

<210> SEQ ID NO 16
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Primer for GDA"
      /organism="Artificial Sequence"

<400> SEQUENCE: 16
caagctgtgg ttgttccatt c                                                  21

<210> SEQ ID NO 17
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Primer for IL36A"
      /organism="Artificial Sequence"

<400> SEQUENCE: 17
cgaggaagga ccgtatgtct                                                    20

<210> SEQ ID NO 18
<211> LENGTH: 21
<212> TYPE: DNA
```

```
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Primer for IL36A"
      /organism="Artificial Sequence"

<400> SEQUENCE: 18
tgagtccatt caggcccagg t                                              21

<210> SEQ ID NO 19
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Primer for TGM1"
      /organism="Artificial Sequence"

<400> SEQUENCE: 19
tcgaaggctc tgggttacag a                                              21

<210> SEQ ID NO 20
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Primer for TGM1"
      /organism="Artificial Sequence"

<400> SEQUENCE: 20
acgactggcg cagtgtcact                                                20

<210> SEQ ID NO 21
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="Primer for CLEC4G"
      /organism="Artificial Sequence"

<400> SEQUENCE: 21
gaagcagacg gcggcgctgg gt                                             22

<210> SEQ ID NO 22
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Primer for CLEC4G"
      /organism="Artificial Sequence"

<400> SEQUENCE: 22
tctcctgctc catcagcttc                                                20

<210> SEQ ID NO 23
<211> LENGTH: 22
```

```
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="Primer for IL13"
      /organism="Artificial Sequence"

<400> SEQUENCE: 23
gagctcattg aggagctggt ca                                              22

<210> SEQ ID NO 24
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Primer for IL13"
      /organism="Artificial Sequence"

<400> SEQUENCE: 24
catgccagct gtcaggttga t                                               21

<210> SEQ ID NO 25
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="Primer for TCN1"
      /organism="Artificial Sequence"

<400> SEQUENCE: 25
gtcaaccact tcactcctg                                                  19

<210> SEQ ID NO 26
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Primer for TCN1"
      /organism="Artificial Sequence"

<400> SEQUENCE: 26
aggacagcca ttgcaccagt a                                               21

<210> SEQ ID NO 27
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Primer for TMPRSS11D"
      /organism="Artificial Sequence"

<400> SEQUENCE: 27
agaatccttg gaggcactga                                                 20

<210> SEQ ID NO 28
```

```
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Primer for TMPRSS11D"
      /organism="Artificial Sequence"

<400> SEQUENCE: 28
gcagtagagc caggtggaat                                                    20

<210> SEQ ID NO 29
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer for RHCG"
      /organism="Artificial Sequence"

<400> SEQUENCE: 29
cagctgctca tcatgacttt cttcc                                              25

<210> SEQ ID NO 30
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="unassigned DNA"
      /note="Primer for RHCG"
      /organism="Artificial Sequence"

<400> SEQUENCE: 30
ctgtctctcc ttgctctgct ctaggt                                             26
```

DIFFERENTIAL DIAGNOSIS OF ECZEMA AND PSORIASIS

The present application is divisional of Ser. No. 15/304,364 filed Oct. 14, 2016 which is U.S. National Phase of PCT/EP2015/058149 filed on Apr. 15, 2015 which claims priority to European patent application No. 14164807.1 filed on Apr. 15, 2014. The disclosure of the PCT Application is hereby incorporated by reference into the present application.

The present invention relates to a method of diagnosing eczema and/or psoriasis, wherein said method differentiates between eczema and psoriasis, and comprises determining the expression of at least two markers in a sample taken from an individual, wherein said at least two markers are selected from CCL27, NOS2, IL36G, KLK13, SOST, NPTX1, PLA2G4D, GDA, IL36A, TGM1, CLEC4G, IL13, TCN1, TMPRSS11D and RHCG, provided that said at least two markers consist of or comprise (a) CCL27 and NOS2; (b) CCL27 and KLK13; (c) IL36G and KLK13; (d) CCL27 and IL36G; (e) NOS2 and IL36G; (f) NOS2 and KLK13; (g) SOST; or (h) NPTX1; and assessing on the basis of the expression of said at least two markers whether the individual is afflicted with eczema and/or psoriasis.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Psoriasis and eczema are prevalent inflammatory skin diseases with high individual disease-burden and major socio-economic impact (Bieber T, Atopic dermatitis. N Engl J Med 358, 1483-94 (2008), Nestle F O et al., N Engl J Med 361, 496-509 (2009)). In recent years, numerous specific therapies were evaluated for both diseases. However, most clinical studies were empiric and not directly related to the increased basic knowledge of disease pathogenesis.

Interestingly, psoriasis and eczema respond differently, sometimes antipodal, to specific therapy regimes (Eyerich K et al., Allergy 68, 974-82 (2013), Guttman-Yassky E et al., J Allergy Clin Immunol 127, 1420-8 (2011)). More specifically, it was demonstrated in patients which suffer from both psoriasis and atopic eczema that anti-TNFα medicaments, which are typically applied in the treatment of psoriasis, do improve the patient's condition with regard to psoriasis, however, at the same time the eczema deteriorates (Eyerich S et al., N Engl J Med 365, 231-8 (2011)). As regards atopic eczema on the other hand, there is no approved specific therapy at the moment. Dupilumab is anti-IL-4 receptor antibody which is currently in phase 3 clinical trials. This monoclonal antibody blocks the effects of IL-4 and IL-13. On the other hand, it is known that IL-4 itself is a useful therapy of psoriasis (Ghoreshi K et al. Nat Med 9, 40-6 (2003)). Therefore, also in such a setting it is to be expected that the treatment which ameliorates eczema will have a negative impact on psoriasis. This problem is further aggravated by the fact that for a significant fraction of patients a clear distinction between psoriasis and eczema is not possible, even for experienced clinicians, the reason being that either disease may manifest itself in different forms, wherein the established clinical parameters may fail to correctly distinguish between certain forms of eczema and certain forms of psoriasis.

Thus, a prerequisite for personalized medicine is a detailed understanding of the molecular mechanisms underlying both diseases.

Although basic knowledge of both conditions increased throughout recent years, our understanding of their molecular basis is still not complete. Novel high-throughput techniques investigating the whole genome expression in biologic material such as microarrays are a useful tool to gain insight into pathogenesis (Suarez-Farinas M et al., J Allergy Clin Immunol 127, 954-64 (2011), Tian S et al., PLoS One 7, e44274 (2012), Suarez-Farinas M et al., J Invest Dermatol 132, 2552-64 (2012)). Previous attempts to use gene expression analysis for comparing psoriasis and atopic eczema were hampered by the high inter-individual variability that is partially based upon gender, age, and short-term environmental exposure prior to material sampling (Wenzel J et al., J Invest Dermatol 128, 67-78 (2008), Nomura I et al., J Allergy Clin Immunol 112, 1195-202 (2003), de Jongh G J et al., J Invest Dermatol 125, 1163-73 (2005)). In fact, Nomura et al. (loc. cit.), while observing distinct patterns of gene expression in the skin lesions of atopic dermatitis and psoriasis. merely suggest that such observations may contribute to a "characteristic signature" for these two skin diseases. A classifier, let alone a validated classifier is not provided. Wenzel et al. (loc. cit.), while investigating inter alia also into atopic dermatitis and psoriasis, is actually concerned with a different issue, namely to provide a distinction between Lichen planus on the one hand and atopic dermatitis and psoriasis on the other hand.

Guttman-Yassky E et al. (J Allergy Clin Immunol 124, 1235-1244 (2009)) and Kamsteeg M et al. (Br J Dermatol 162, 568-578 (2010)) describe classifiers to be used in distinguishing between atopic dermatitis and psoriasis based on gene expression levels. The classifier of Guttman-Yassky et al. (loc. cit.) requires thirteen genes and that of Kamsteeg et al. (loc. cit.) seven genes. Independent validation of the respective classifier with patient data not used for training is not provided.

The technical problem underlying the present invention can be seen in the provision of alternative and improved means and methods for diagnosing psoriasis and eczema, wherein such means and methods are capable of differentiating between these two diseases.

In the first aspect, the present invention relates to a method of diagnosing eczema and/or psoriasis, wherein said method differentiates between eczema and psoriasis, and comprises determining the expression of at least two markers in a sample taken from an individual, wherein said at least two markers are selected from CCL27, NOS2, IL36G, KLK13, SOST, NPTX1, PLA2G4D, GDA, IL36A, TGM1, CLEC4G, IL13, TCN1, TMPRSS11D and RHCG, provided that said at least two markers consist of or comprise (a) CCL27 and NOS2; (b) CCL27 and KLK13; (c) IL36G and KLK13; (d) CCL27 and IL36G; (e) NOS2 and IL36G; (f) NOS2 and KLK13; (g) SOST; or (h) NPTX1; and assessing on the basis of the expression of said at least two markers whether the individual is afflicted with eczema and/or psoriasis.

Related thereto, the present invention relates to a method of diagnosing eczema and/or psoriasis, wherein said method differentiates between eczema and psoriasis, and comprises determining the expression of at least two markers in a sample taken from an individual, wherein said at least two markers are selected from CCL27, NOS2, IL36G, KLK13, SOST. NPTX1, PLA2G4D, GDA, IL36A, TGM1, CLEC4G, IL13, TCN1, TMPRSS11D and RHCG, provided that said at least two markers consist of or comprise (a)

CCL27 and NOS2; (b) CCL27 and KLK13; (c) IL36G and KLK13; (d) CCL27 and IL36G; (e) NOS2 and IL36G; (f) NOS2 and KLK13; (g) SOST; or (h) NPTX1.

Psoriasis and eczema are inflammatory skin diseases known to the clinician; see introductory section above and references cited there.

The term "expression" has its art-established meaning and defines, in a quantitative sense, the degree of transcription and/or translation of a given gene. Accordingly, it is understood that the method of diagnosing according to the first aspect of the present invention may, in preferred embodiments, employ mRNA expression data and/or protein expression data. Means and methods for determining expression data are detailed further below.

As stated above, the method of diagnosing employs at least two markers to be selected from the list of fifteen markers presented above, wherein furthermore one of the requirements (a) to (h) has to be met. Accordingly, it is understood that the language "said at least two markers comprise" relates to any one of items (a) to (h), and the language "said at least two markers consist of" relates to any one of items (a) to (f).

Preferably, only two markers are used. While also three, four, five, six, seven, eight, nine, ten, eleven, twelve, thirteen, fourteen or the whole set of fifteen markers may be used, it is a surprising achievement of the present inventors to provide very small sets of markers, namely two markers, which—despite the small size of the set—yield excellent classifiers to be used in the assessment whether the individual is afflicted with eczema and/or psoriasis. Their good performance has been cross-validated, i.e. by testing them on data sets which were not used for training. This is an important distinction from the prior art which not only uses larger sets of markers, but also fails to independently cross-validate the respective classifier.

Accordingly, while it is envisaged that, for example, the group of two markers consisting of CCL27 and NOS2 may be expanded by adding one or more markers from the thirteen remaining markers of the list of fifteen provided above, it is particularly preferred to exclusively use the expression of CCL27 and NOS2 for the purpose of diagnosing eczema and/or psoriasis and furthermore differentiating between these two diseases.

The gene names used in the definition of the first aspect of the present invention are standard art-established gene names. Table 1 below provides the full names and functional annotations of these genes.

TABLE 1

15 genes that distinguish psoriasis and eczema.

| Gene | Full name | Function | Category |
|---|---|---|---|
| SOST | sclerostin | Inhibition of Wnt signaling | Metabolism |
| PLA2G4D | phospholipase A2, group IVG | Widespread metabolic functions | Metabolism |
| IL36G | interleukin-36G | Induces epidermal proliferation and AMPs | Immune System |
| NOS2 | inducible nitric oxide synthase 2 | Stress-induced molecule with multiple functions on immune and metabolic processes | Metabolism, Immune System |
| KLK13 | kallikrein-related peptidase 13 | Induction of AMPs in the skin | Immune System |
| GDA | guanine deaminase | Involved in purine metabolism | Metabolism |
| IL36A | interleukin-36A | Induces epidermal proliferation and AMPs | Immune System |
| TGM1 | transglutaminase 1 | Formation of the cornified envelope | Epidermis |
| NPTX1 | neuronal pentraxin 1 | Involved in neuronal metabolism and damage | Metabolism |
| CCL27 | chemokine (C-C motif) ligand 27 | Binds to CCR10, promotes lymphocytes migration into the skin | Epidermis, Immune System |
| CLEC4G | C-type lectin family member 4 | Inhibits activation of CD4+ T cells | Immune system |
| IL13 | interleukin-13 | Acts on epithelium (inhibition of AMPs, induction of fibrosis, induction of chemokines) and on macrophages | Immune system |
| TCN1 | transcobalamin1 | Vitamine B12 binding | Metabolism |
| TMPRSS11D | serine transmembrane protease 11D | Preform of macrophage activating molecule | Immune System |
| RHCG | RH family, C glycoprotein | Ammonia transporter | Metabolism |

FIG. 1A presents the expression data (mRNA levels) of the fifteen genes for the two diseases and furthermore gene specific cut-offs separating expression levels characteristic of psoriasis from those characteristic of eczema. Cut-off values are also given in Table 2 below.

TABLE 2

Statistical analysis of genes included into the disease-classifier to distinguish psoriasis and eczema. Given are the names of the genes, p-values, sensitivity, specificity, positive likelihood ratio and cut-off values obtained from Real-time PCR analysis of the training cohort as part of the independent cohort (n = 19).

| Gene | p-value | Sensitivity (%) | Specificity (%) | Positive likelihood ratio | Cut-off value (fold induction) |
|---|---|---|---|---|---|
| NOS2 | 1.5396 * 10<sup>−6</sup> | 100 | 88.89 | 9 | 1.584 |
| TMPRSS1 | 0.0201 | 90 | 88.89 | 8.1 | 2.304 |
| RHCG | 0.0185 | 100 | 88.89 | 9 | 1.364 |
| SOST | 0.0017 | 90 | 88.89 | 8.1 | 0.9391 |
| TCN1 | 0.0995 | 80 | 77.78 | 3.6 | 2.398 |
| GDA | 0.0071 | 70 | 88.89 | 6.3 | 0.999 |
| IL36A | 0.3598 | 60 | 77.78 | 2.7 | 2.868 |
| IL36G | 0.0014 | 90 | 88.89 | 8.1 | 1.219 |
| KLK13 | 0.0248 | 100 | 88.89 | 9 | 1.05 |
| PLAG4D | 0.0254 | 90 | 88.89 | 8.1 | 1.081 |
| TGM1 | 0.0876 | 70 | 88.89 | 6.3 | 0.8832 |
| IL13 | 0.5749 | 40 | 77.78 | 1.8 | 0.7974 |
| CLEC4G | 0.3521 | 60 | 88.89 | 5.4 | 0.2029 |
| CCL27 | 0.0005 | 80 | 88.89 | 7.2 | −0.3983 |
| NPTX1 | 0.02001 | 80 | 88.89 | 7.2 | −0.4779 |

TABLE 3

Database entries (GenBank release 200.0 of Feb. 15, 2014; Ensemble release 75 of February 2014) for the 15 markers of the invention.

| Systematic Name | Entrez ID | Symbol |
|---|---|---|
| NM_000625 | 4843 | NOS2 |
| NM_015596 | 26085 | KLK13 |
| NM_004293 | 9615 | GDA |
| NM_006664 | 10850 | CCL27 |
| NM_001062 | 6947 | TCN1 |
| NM_025237 | 50964 | SOST |
| ENST00000441527 | 26085 | KLK13 |
| NM_002188 | 3596 | IL13 |
| NM_004262 | 9407 | TMPRSS11D |
| NM_014440 | 27179 | IL36A |
| NM_198492 | 339390 | CLEC4G |
| NM_016321 | 51458 | RHCG |
| NM_019618 | 56300 | IL36G |
| NM_000359 | 7051 | TGM1 |
| NM_002522 | 4884 | NPTX1 |

Surprisingly, the most preferred classifier, i.e. the method of diagnosing according to the first aspect, wherein said at least two markers are exactly two markers which are CCL27 and NOS2, yields correct results where the established diagnostic gold standard, namely visual inspection of the patient by the experienced clinician and histological analysis fail. In particular, the predictor classified a patient as suffering from eczema which patient, based on clinical parameters, was initially diagnosed as having psoriasis. Only the initially surprising result delivered by the method according to the present invention prompted the clinicians to go back and review once more clinical and histological features of this patient. In particular, the therapy initially chosen and targeted at psoriasis did not improve the patient's condition, thereby confirming that clinical diagnosis was wrong and the method of the present invention correct.

A second case of particular interest was a patient which, from clinical and histological aberration, could not be assigned unambiguously. In other words, established methods failed to distinguish between psoriasis and eczema. The classifier according to the present invention instead clearly established eczema. Both of the above described special cases are further detailed in the examples enclosed herewith.

Given that either disease can be diagnosed with a high degree of certainty when using the methods according to the present invention, also patients suffering from both diseases will benefit. More specifically, for those patients the recommendation can be given that therapies which ameliorate one disease but cause worsening of the other are to be avoided. Instead, recourse has to be taken in such cases to more conventional therapies which work less specific and provide alleviation in either case. These conventional therapies are well-known in the art and include steroids.

The present inventors' investigations into differential gene expression between psoriasis and eczema, while primarily aiming to provide compact and reliable classifiers, also yield an insight into the molecular and cellular mechanisms underlying the respective disease: see Example 2.

While particular preference is given to the use of exactly two markers, the present invention also provides larger sets of markers. Two particularly preferred groups of three markers are given below. In other words, in a preferred embodiment, said at least two markers are at least three markers and consist of or comprise: (i) CCL27, NOS2 and IL36G; or (j) CCL27, KLK13 and IL36G.

A key aspect of the present invention is the identification and validation of particularly small and particularly powerful sets of markers. This is defined by the embodiments disclosed above. Once the sets of markers to be used being established, various methods are at the skilled person's disposal to make use of the markers for diagnostic purposes, namely the assessment whether the individual is afflicted with eczema and/or psoriasis.

In a preferred embodiment, said diagnosing is effected by a classifier.

The term "classifier" has its art-established meaning and refers to a computer-implemented algorithm. Said algorithm, when fed with patient data (in the present case expression levels) yields an output which assigns the respective patient either to the group of psoriasis patients or the group of eczema patients. Thus, assessment whether the individual is afflicted with eczema and/or psoriasis is preferably effected by a classifier.

While preference is given to the method according to the first aspect being confined to such classifier-based diagnosis, it is understood that the results provided by the method of the first aspect, preferably by said classifier, may be compared, complemented or validated by established clinical methods, in particular visual inspection of the patient and/or histological analysis of a sample taken from the patient. Histological hallmarks of psoriasis on the one hand and eczema on the other hand, in particular in clear-cut cases (which, as noted above, does not apply to all patients) are well-known in the art; see, for example, Bieber (loc. cit.) and Nestle (loc. cit.).

In a more preferred embodiment, (a) said classifier is obtainable by analyzing said expression of said at least two markers in samples taken from individuals suffering from eczema and in samples taken from individuals suffering from psoriasis; or (b) said method further comprises calculating said classifier by analyzing said expression of said at least two markers in samples taken from individuals suffering from eczema and in samples taken from individuals suffering from psoriasis.

Accordingly, the method of the present invention may optionally further comprise the step of building said classifier, or, in the alternative, may make use of a previously established classifier.

Given that the specific and advantageous selection of markers according to the first aspect of the present invention avoids the above discussed problems arising from patient-specific genetic background, training of the classifier in accordance with item (b) does not pose particular challenges with regard to the choice of patients the samples of which are to be used for classifier training. Preference is given to patients with clear-cut clinical symptoms of the respective disease. Preferred are furthermore large cohorts of patients.

In a particularly preferred embodiment, wherein said analyzing is by means of support vector machines (SVMs), generalized linear models (GLMs), linear discriminant analysis, decision trees, decision rules, neural networks, Bayes regression methods, and/or nearest neighbor methods; see, e.g. Bishop (Pattern Recognition and Machine Learning (Information Science and Statistics), Springer, ISBN: 0387310738 (2007)). Particularly preferred are SVMs.

Preferably, expression data is normalized prior to analysis. Normalization can be effected by dividing expression data for a given marker from a diseased sample by the expression level of the same marker from a healthy sample. In either case, averages are preferred. Furthermore, it is preferred to use the logarithms of the expression levels (see, for example, FIG. 1).

In a particularly preferred embodiment, a linear SVM is used, wherein, to the extent mRNA expression data are used, it is most preferred that the negative intercept (rho) is given by 0.22 with a 99% confidence interval (CI) of [−1.24, 0.89]. The corresponding parameters to scale the data for the linear SVM and the weight vector are given as follows:

|  | NOS2 | CCL27 |
| --- | --- | --- |
| center | 0.84 [0.25, 1.46] | −0.47 [−0.87, −0.13] |
| scale | 1.15 [0.86, 1.37] | 0.7 [0.48, 0.84] |
| w | 1.7 [−2.14, 2.13] | −0.32 [−0.63, 0.63] |

With the 99% CI given in brackets and the labels of psoriasis: 1 and atopic eczema: −1.

Also preferred is to use the information of FIG. 1B as enclosed herewith or FIG. 1B as such for classification purposes. To explain further, upon determining the normalized mRNA expression levels of NOS2 and CCL27 of a patient to be classified, said patient is classified by determining whether its expression data fall into the area labelled "psoriasis" or into the area labelled "eczema".

In a further preferred embodiment, said eczema is selected from atopic eczema (also known as atopic dermatitis), contact dermatitis, nummular dermatitis and dyshidrotic eczema. The method of the present invention successfully distinguishes any of the mentioned specific forms of eczema from psoriasis.

In a further preferred embodiment, said psoriasis is selected from psoriasis vulgaris, psoriasis inversa and psoriasis *pustulosa*.

In a further preferred embodiment, said expression is expression (a) at the mRNA level and/or (b) at the protein level.

In a particularly preferred embodiment, said determining is effected by PCR, preferably real-time PCR. PCR is used for determining the mRNA level. Preferred primers to be used are disclosed further below in conjunction with kits of the present invention.

PCR is well known in the art and is employed to make large numbers of copies of a target sequence. PCR comprises three major steps, which typically are repeated for 30 or 40 cycles. This is done on an automated cycler device, which can heat and cool containers with the reaction mixture in a very short time. The first step is denaturation, e.g. at 94° C. During the denaturation, the double strand melts to form single stranded DNA. Concomitantly, all enzymatic reactions are stopped. These enzymatic reactions include, for example, the extension reaction of a previous PCR cycle. The second step is annealing, e.g. at 54° C. Bonds are constantly formed and broken between the single stranded primer and the single stranded template. The more stable bonds last a bit longer (primers that match exactly) and on the formed double stranded DNA comprising template and primer, the polymerase can attach and starts copying the template. Once a few bases are built in, the bonds are sufficiently strong between the template and the primer such that it does not break anymore. The third step is an extension step which is performed at a temperature of, for example, 72° C. This is the ideal temperature for polymerase activity. The primers, where there are a few bases built in, already exhibit a stronger binding to the template as compared to primers that are on positions with no exact match, which in turn get loose again (because of the higher temperature as compared to the annealing step) and do not give rise to an extension of the fragment.

Real-time PCR is a specific type of PCR, where the process of amplification can be monitored directly and in real time, which permits a significantly more precise determination of expression levels than conventional end-point PCR. It may either employ a specific probe, in the art also referred to as TaqMan probe, which has a reporter dye covalently attached at the 5' end and a quencher at the 3' end. After the TaqMan probe has been hybridized in the annealing step of the PCR reaction to the complementary site of the polynucleotide being amplified, the 5' fluorophore is cleaved by the 5' nuclease activity of Taq polymerase in the extension phase of the PCR reaction. This enhances the fluorescence of the 5' donor which was formerly quenched due to the close proximity to the 3' acceptor in the TaqMan probe sequence. Alternatively, specific primers may be combined with a fluorescent dye (SYBR green) that binds to double stranded DNA. By specific gene amplification, double stranded DNA is formed and can be measured via the increase of fluorescence in the PCR mix.

In a further particularly preferred embodiment, said determining is effected by antibodies, in particular by antibodies which are specific for the given marker protein. Antibodies are preferably used for determining the above mentioned protein level.

Antibodies may be labeled, or bound antibodies may in turn be detected by using labeled (secondary) antibodies. Preferred labels are fluorescent, luminescent and radioactive labels. Particularly preferred are fluorescent labels. The latter type of detection scheme is also known in the art as immunofluorescence. A further art-established alternative are enzyme-linked immunosorbent assays (ELISA).

The term "antibody" includes monoclonal antibodies, polyclonal antibodies, single chain antibodies, or fragments thereof that specifically bind said peptide or polypeptide, also including bispecific antibodies, synthetic antibodies, antibody fragments, such as Fab. a F(ab$_2$)', Fv or scFv fragments etc., or a chemically modified derivative of any of these. Monoclonal antibodies can be prepared, for example, by the techniques as originally described in Köhler G and Milstein C, Nature 256 495-7 (1975), and Galfré G and Milstein C, Meth. Enzymol. 73 3-46 (1981), which comprise the fusion of mouse myeloma cells to spleen cells derived from immunized mammals with modifications developed by the art. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of the peptide or polypeptide of the invention (Schier, Human Antibodies Hybridomas 7 97-105 (1996); Malmborg, J. Immunol. Methods 183 7-13 (1995)). The production of chimeric antibodies is described, for example, in WO89/09622. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art: see, e.g., Sambrook, Molecular Cloning: A Laboratory Manual, Cold Spring Harbor Laboratory, Cold Spring Harbor, NY, 1989.

The term "monoclonal" or "polyclonal antibody" (see Harlow and Lane, (1988), loc. cit.) also relates to derivatives of said antibodies which retain or essentially retain their binding specificity. Whereas particularly preferred embodiments of said derivatives are specified further herein below, other preferred derivatives of such antibodies are chimeric antibodies comprising, for example, a mouse or rat variable region and a human constant region.

The term "scFv fragment" (single-chain Fv fragment) is well understood in the art and preferred due to its small size and the possibility to recombinantly produce such fragments.

Preferably, the antibody, fragment or derivative thereof specifically binds the target protein. The term "specifically binds" in connection with the antibody used in accordance with the present invention means that the antibody etc. does not or essentially does not cross-react with (poly)peptides of similar structures. Cross-reactivity of a panel of antibodies etc. under investigation may be tested, for example, by assessing binding of said panel of antibodies etc. under conventional conditions (see, e.g., Harlow and Lane, (1988), loc. cit.) to the (poly)peptide of interest as well as to a number of more or less (structurally and/or functionally) closely related (poly)peptides. Only those antibodies that bind to the (poly)peptide/protein of interest but do not or do not essentially bind to any of the other (poly)peptides which are preferably expressed by the same tissue as the (poly)peptide of interest, are considered specific for the (poly)peptide/protein of interest.

In a particularly preferred embodiment of the method of the invention, said antibody or antibody binding portion is or is derived from a human antibody or a humanized antibody. The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A1 0 239 400 and WO90/07861.

As such either method, be it PCR or determining by antibodies is well-established in the art. The antibody is preferably labeled or is to be detected by labeled compounds such as labeled secondary antibodies. Given that tissue sections from psoriasis and eczema patients are generally available to the clinician, immunohistochemistry and/or immunofluorescence are particularly suitable methods of determining and quantifying protein expression by means of antibodies.

In a further preferred embodiment, said sample is a skin sample affected by the disease such as a slice of skin or a skin biopsy affected by the disease. Slices may be obtained by using a microtome.

Typically, said sample is preprocessed in order to obtain a homogenous phase. Determining expression of at least two markers is then effected in said homogenous phase.

Surprisingly, the present inventors discovered that classifying, or, more generally, diagnosing can also be effected directly on a stained skin sample such as a skin biopsy or a slice of skin. Staining is preferably obtained by the above disclosed method employing antibodies. In accordance with this approach, a stained skin sample is subjected to image analysis. For exemplary implementations using either Fourier transformation and/or convolution, reference is made to Example 6.

Accordingly, and to the extent said sample is a skin sample and said expression is a expression at the protein level, (i) said determining the expression is effected by staining of said skin sample; and (ii) said diagnosing is effected by image analysis of the stained skin sample.

In other words, morphological distribution, in particular morphological distribution at a level of cellular morphology of markers in accordance with the present invention may be used for the purpose of diagnosing. Staining is preferably effected by immunofluorescence, preferably of slices of skin. Image analysis preferably involves Fourier transformation and/or convolution.

As noted above, both eczema and psoriasis are inflammatory skin diseases which generally effect part, but not all of the skin of a given patient. For the purpose of determining disease-specific expression, choosing disease affected skin samples is the method of choice.

In a further preferred embodiment, said individual is Caucasian.

In a second aspect, the present invention provides a kit comprising or consisting of means for quantifying the expression of at least two markers selected from CCL27, NOS2, IL36G, KLK13, SOST, NPTX1, PLA2G4D, GDA, IL36A, TGM1, CLEC4G, IL13, TCN1, TMPRSS11D and RHCG, provided that said at least two markers consist of or comprise (a) CCL27 and NOS2; (b) CCL27 and KLK13; (c) IL36G and KLK13; (d) CCL27 and IL36G; (e) NOS2 and IL36G; (f) NOS2 and KLK13; (g) SOST; or (h) NPTX1.

In a preferred embodiment, said means are primers, wherein the primers for the respective genes are as follows: CCL27: SEQ ID NOs: 1 and 2; NOS2: SEQ ID NOs: 3 and 4; IL36G; SEQ ID NOs: 5 and 6; KLK13: SEQ ID NOs: 7 and 8; SOST: SEQ ID NOs: 9 and 10; NPTX1; SEQ ID NOs: 11 and 12: PLA2G4D: SEQ ID NOs: 13 and 14: GDA: SEQ ID NOs: 15 and 16; IL36A: SEQ ID NOs: 17 and 18; TGM1: SEQ ID NOs: 19 and 20; CLEC4G: SEQ ID NOs: 21 and 22; IL13: SEQ ID NOs: 23 and 24; TCN1: SEQ ID NOs: 25 and 26; TMPRSS11D: SEQ ID NOs: 27 and 28; RHCG: SEQ ID NOs: 29 and 30.

In a further preferred embodiment, said means are antibodies which are specific for the given marker protein.

In a further preferred embodiment, said kit further comprises one or more of the following: (a) means for obtaining a skin sample; (b) means for isolating or enriching RNA from a skin sample; (c) means for performing PCR: and (d) means for preparing tissue sections.

In a further preferred embodiment, the kit according to the second aspect of the present invention further comprises a manual comprising instructions for performing the method of the first aspect of the present invention.

In a third aspect, the present invention provides use of at least two markers selected from CCL27, NOS2, IL36G, KLK13, SOST, NPTX1, PLA2G4D, GDA, IL36A, TGM1, CLEC4G, IL13, TCN1, TMPRSS11D and RHCG, provided that said at least two markers consist of or comprise (a) CCL27 and NOS2; (b) CCL27 and KLK13; (c) IL36G and KLK13; (d) CCL27 and IL36G; (e) NOS2 and IL36G; (f) NOS2 and KLK13; (g) SOST; or (h) NPTX1 for diagnosing eczema and/or psoriasis in a sample taken from an individual.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H: B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The Figures Show:

FIG. 1

A Real-time PCR validation of 15 genes significantly different between psoriasis (n=9) and eczema (n=10). The curve shows the cut-off values between the two groups for each gene. Frames indicate the two genes chosen to build up the disease classifier. *=p<0.05, p<0.01, *p<0.0001, no star p<0.1 (Bonferroni corrected for multiple testing. B A disease classifier consisting of NOS2 (y-axis) and CCL27 (x-axis) accurately separates psoriasis and eczema patients in a training set consisting of 19 patients (9 psoriasis, 10 eczema). Shown are data samples of the training set after log transformation and scaling. The crosses indicate the support vectors, the circles indicate the remaining data samples of the training set. C Performance of the disease classifier in an independent test cohort (16 psoriasis patients, 18 eczema patients). The square shows one initially mis-classified patient, the squares with discontinued contour a clinically and histologically unclear patient illustrated in D. Scale bars indicate 100 µm in overview and 50 µm in islets, respectively.

FIG. 2

Immunofluorescence stainings for DAPI, NOS2, and CCL27 of eczema and psoriasis skin.

FIG. 3

CCL27 staining pattern distinguishes psoriasis from eczema.

The Examples illustrate the invention.

EXAMPLE 1

Classifier Build Up 15 marker genes were selected according to the following criteria: genes with most predominant difference between psoriasis and eczema; and functional annotation as epidermal, immune related, and metabolic genes.

For training the classifier on the real-time PCR data of an independent disease cohort (n=19), the R package "e1071" (http://CRAN.R-project.org/package=e1071) was applied using support vector machines (SVMs). To get normally distributed data the measurements of the selected 15 genes were transformed using the logarithm to the base 10. Then, a two-sample, two-sided Welch's t-test followed by a Bonferroni p-value correction was used to test for differential expression. The two genes which were most significantly down-regulated (CCL27, adjusted p-value=$5.31*10^{\wedge}(-4)$), or up-regulated (NOS2, adjusted p-value=$1.53*10^{\wedge}(-6)$) were selected for the preferred classifier. The scaled and log transformed data of the two genes were used as a training set for a C-classification using a linear kernel function with C=1. To train the classifier a 10-fold cross-validation was used. Then, the classifier was tested on log-transformed data samples of a third independent cohort (n=34) by predicting the disease class and computing probability predictions based on the trained model.

Primer Design and Real-Time PCR

Primers amplifying genes of interest were designed using the publicly accessible Primer3 software (http://frodo.wi.m-it.edu/primer3/). The used primers are given in the sequence listing.

Real time PCR reactions were performed in 384-well plates using the Fast Start SYBR Green Master mix (Roche Applied Science) and the ViiA7 Real Time PCR machine (Applied Biosystems). The expression of transcripts was normalized to expression of 18S ribosomal RNA as housekeeping gene. Data were expressed as mRNA fold change, relative to non-involved skin as calibrator. Relative quantification was determined according to the formula: $(RQ)=2^{-\Delta\Delta C_1}$.

EXAMPLE 2

Function of Uniquely Regulated Genes

Concerning the immune system, differences between psoriasis and eczema were observed: exclusively in psoriatic skin, cytokines belonging to the IL-10 family such as IL-19 and IL-20 as well as IL-36A and IL-36G were significantly up-regulated. A non-significant trend for a higher induction of Th17 associated cytokines IL-17A, IL-17F, IL-21, and IL-22 was also observed in psoriatic plaques. Cytokines that were exclusively induced in eczematous lesions were IL-6 and the Th2 cytokine IL-13, with a trend for a higher induction of other Th2 cytokines IL-4, IL-5, and IL-10 in eczematous as compared to psoriatic skin.

The chemokines CCL17 and CCL18 were up-regulated in eczematous lesions to a higher degree than in psoriatic skin. CCL27 was down-regulated significantly in psoriatic skin. On the other hand, CXCL1 and CXCL8 (IL-8) showed a stronger up-regulation in psoriatic plaques, with CXCL8 being exclusively regulated in psoriatic skin.

Bridging the immune system and the epidermal component, numerous antimicrobial peptides (AMPs) were found to be up-regulated in both psoriatic and eczematous skin as compared to non-involved skin, respectively. The defensin members DEFB4 and DEFB103B as well as the S100 proteins S100A7A, S100A7, S100A8, S100A9, and S100A12 were significantly up-regulated in both diseases. However, induction of all detected AMPs was much higher in psoriatic than in eczematous skin. Accordingly, the IL-20 induced Kallikrein-related peptidases KLK6, KLK9, and KLK13, demonstrated to induce AMPs, were exclusively up-regulated in psoriatic, but not in eczematous skin.

Differences were also observed regarding early differentiation markers of the small proline-rich protein (SPRR) family and the late cornified envelope (LCE) family. SPRR1A, SPRR1B, SPRR2A, SPRR2B, SPRR2C, SPRR2D, LCE3C, and comifelin were exclusively up-regulated in psoriatic plaques. LCE3A, LCE3D, and LCE3E were up-regulated in both psoriasis and eczema skin, but to a higher degree in psoriasis. In contrast, LCE1B, and LCE5A were down-regulated both in psoriatic and eczematous skin, but to a higher degree in eczema. A heterogeneous picture was observed regarding keratin regulation, with KRT6A, KRT6B, KRT6C, KRT16 and KRT75 highly up-regulated in psoriatic skin and KRT2, KRT19 as well as KRT77 down-regulated more in psoriatic than in eczematous skin. The late differentiation genes of the filaggrin family FLG and FLG2 were also down-regulated in both psoriatic and eczematous skin. hornerin was up-regulated more in psoriatic than in eczematous as compared to non-involved skin.

Numerous genes involved in glucose, lipid, and amino acid metabolism were exclusively regulated in psoriatic, but not in eczematous skin. Namely, regulation of the phospholipase PLA2G4D, nitric oxide synthase 2 (iNOS or NOS2), ATP-binding cassettes ABCG4, the serine proteases PRSS22, PRSS27, PRSS53, kynureninase, transcobalamin, and the Wnt signaling inhibitor sclerostin were up-regulated exclusively in psoriatic plaques. The aldo-keto reductase family members AKR1B15, AKR1B10 and the peptidase inhibitor PI3 were up-regulated in both psoriatic and eczematous skin, but more in psoriasis.

EXAMPLE 3

Establishing a Disease Classifier to Distinguish Psoriasis and Eczema

Since differences between psoriasis and eczema were observed at both single gene and signaling pathway level, we sought to translate these basic results into a disease classifier that enables to distinguish psoriasis from eczema. The 15 genes of the invention (Table 1, FIG. 1A) were included in a validation cohort with 19 patients (9 for psoriasis, 10 for eczema) to train a classifier. Expression of the selected 15 genes was detected using real-time PCR in all 19 patients and a two-sample, two-sided Welch's t-test on the log-transformed measurements followed by a Bonferroni p-value correction was used to assign each of the 15 genes with a p-value. The primer sequences used for real-time PCR are given in table S4. CCL27 and NOS2 were the genes with lowest adjusted p-values (for significantly up and down regulation, respectively, of psoriasis versus eczema). Based on these two genes a classifier was trained using a 10-fold cross-validation and support vector machines (SVMs). An average accuracy of 100% was achieved (FIG. 1B). With an independent third cohort (34 patients in total; 16 psoriasis patients and 18 eczema patients), the classifier was tested and could classify 33 out of 34 patients as predicted from clinical and histological evaluation (kappa=0.94; FIG. 1C).

EXAMPLE 4

Performance of the Classifier in Special Cases

One patient was classified as eczema with a probability of 0.85, although the given diagnosis was psoriasis. Back-tracing clinical and histological features of this patient revealed that the initial diagnosis psoriasis was most likely not correct. The 54 year old patient presented with disseminated, demarcated eczema-like skin lesions with centripedal desquamation that had erupted two months before. Histological evaluation revealed neutrophil microabscesses, spongiosis, single cell necrosis in the epidermis, and an epidermotropism of immune cells. Other hallmarks for psoriasis such as acanthosis and epidermal thinning above dermal papillae containing dilated and tortuous capillaries were not observed. In line with that observation, the patient did not respond well to dithranol. Furthermore, skin lesions did not relapse after remission. Retrospectively, other diagnoses like *pityriasis rosea*, eczema or *pityriasis* lichenoides chronica are clearly to be favored in this patient.

Besides patients with a given diagnosis from clinical and histological evaluation, one patient was tested where the gold standard methods could not distinguish between psoriasis and eczema (FIG. 1D). The female 53 year-old patient suffered from inflammatory skin lesions since years. Eczema could have been favored because she suffered from allergic asthma, her IgE was mildly elevated (108 IU/ml), and the lesions were itchy; the positive family history for psoriasis and the very stationary plaques in predilection areas were typical rather for psoriasis. Also the histological evaluation was conflicting, with a plump acanthosis, partially missing stratum *granulosum* and parakeratosis accounting for psoriasis. On the other hand, T cell epidermotropism and very few neutrophils with missing microabscesses were more typical for eczema. When this patient was tested in the classifier, the two biopsies were classified as eczema with a probability above 99%, indicating the classifier might be useful even in cases where established gold standard diagnostic tools fail.

EXAMPLE 5

Immunofluorescence

Figure 2:
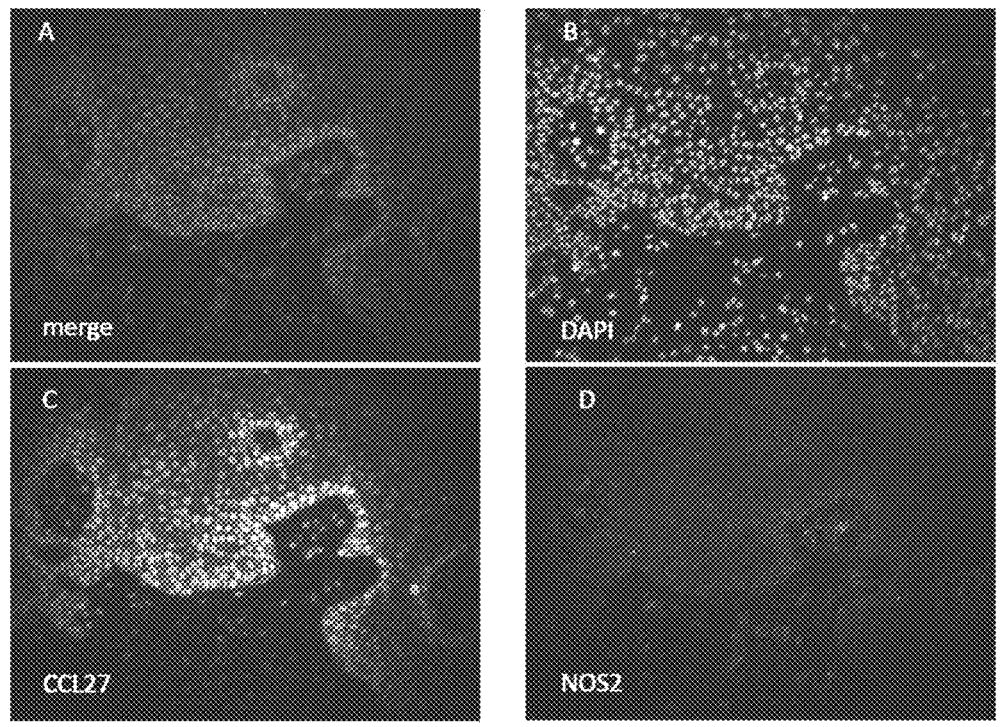
Figure 2:
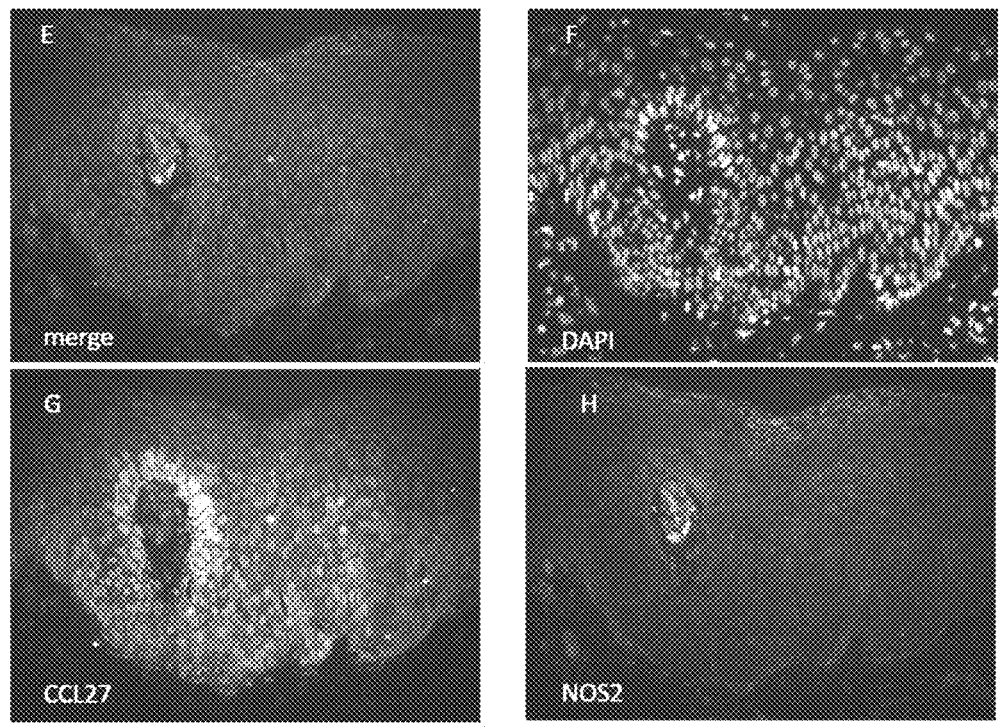

The proposed disease classifier of psoriasis and eczema based on the markers NOS2 and CCL27 is valid at the level of immunofluorescence. This has been confirmed using data from 118 patients. Paraffin-embedded skin biopsies from psoriasis, eczema, and clinically as well as histologically unclear skin lesions were stained for DAPI (nuclear staining), NOS2, and CCL27. In line with the results obtained from PCR analysis at RNA level, psoriasis sections stained strongly positive for NOS2, but hardly for CCL27. In contrast, eczema sections were positive for CCL27, but NOS2 staining was very weak to absent (FIG. 2). In conclusion, the proposed classifier to distinguish psoriasis from eczema is valid at protein expression level, as demonstrated using immunofluorescence double stainings.

EXAMPLE 6

Image Analysis

Figure 3:
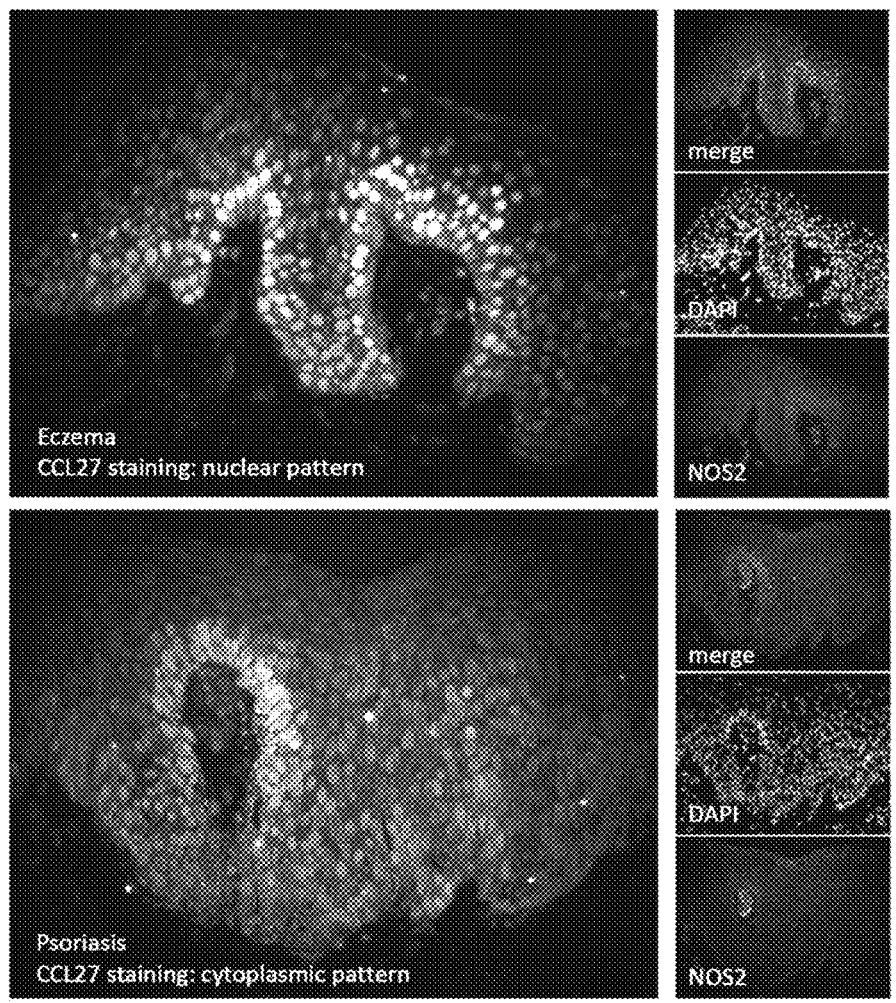
Figure 3:
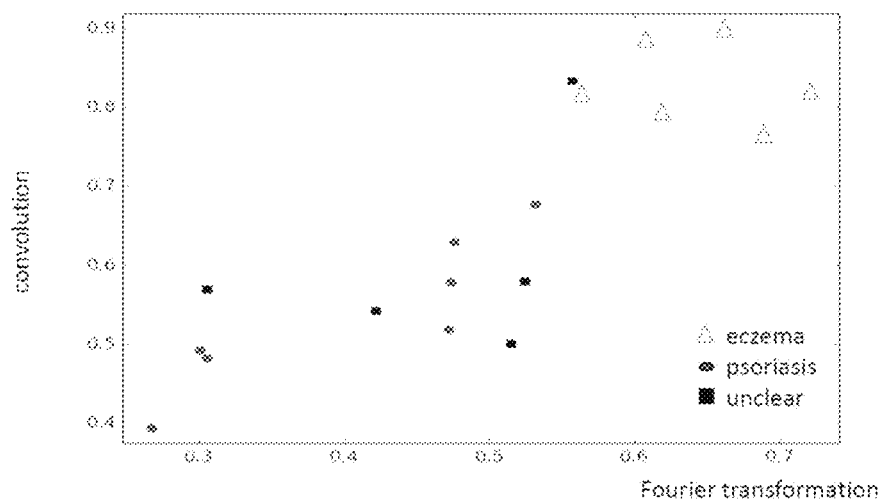

The proposed markers NOS2 and CCL27 allow to distinguish psoriasis from eczema based on their protein expression pattern. In particular, CCL27 distributes homogenously over the cytoplasm in psoriasis sections, while eczema samples are characterized by a clear nuclear staining pattern (FIG. 3).

An image analysis programme was established using Python programming language: Both color channels of each image (blue channel for nuclear stain DAPI and red channel for CCL27 stain) were analysed separately and compared amongst each other using two different methods simultaneously.

The first method is based on Fourier transformation which decomposes an image into its frequencies in a two-dimensional space (sine and cosine components). Sharp edges which can be seen in the DAPI channel as well as in the CCL27 channel of eczema—where clear borders between positive nuclei and rather negative cytoplasm are found—are represented by high frequencies, whereas ubiquitous cytoplasmatic occurrence pf CCL27 as seen in psoriasis is represented by low edges and as such by low frequencies. Similar frequency power densities between the two channels are resulting in quotients close to 1, distinct frequency power densities in quotients close to 0.

The second method is based on convolution. Here, both color channels of each part of the image are sequentially compared with each other in windows of 32×32 pixel. The higher the congruence—which is the case of CCL27 distribution in eczema and DAPI but not between CCL27 distribution in psoriasis and DAPI—the higher the calculated values (maximal value 1, minimal value 0). For each image both values are represented by one dot in a 2 dimensional coordinate system. A line is plotted at maximal separation of both groups.

The invention claimed is:

1. A kit for quantifying the expression of protein from a set of genes in a sample, or a subset thereof, wherein the set of genes is the group consisting of CCL27, NOS2, IL36G, KLK13, SOST, NPTX1, PLA2G4D, GDA, IL36A, TGM1, CLEC4G, IL13, TCN1, TMPRSS11D and RHCG, comprising means for quantifying the expression of protein from at least a subset of the genes consisting of a CCL27 gene and a NOS2 gene, and wherein said means for quantifying expression of the CCL27 gene and means for quantifying expression of the NOS2 gene are antibodies, or fragments thereof, that specifically bind to CCL27 protein and to NOS2 protein, respectively.

2. The kit of claim 1, wherein said subset of genes includes only the CCL27 gene and the NOS2 gene.

3. The kit of claim 1, wherein said antibodies that specifically bind to the proteins are monoclonal antibodies or fragments thereof.

4. The kit of claim 1, wherein said antibodies that specifically bind to the proteins are polyclonal antibodies or fragments thereof.

5. The kit of claim 1, wherein the antibodies that specifically bind to the proteins are labeled.

6. The kit of claim 5, wherein the antibodies are fluorescently-labeled, luminescently-labeled, radioactively-labeled or labeled for ELISA detection.

7. The kit of claim 6, wherein the antibodies are fluorescently labeled.

8. The kit of claim 3, wherein the antibody fragments are any one of a Fab, a F(ab$^2$), a Fv or a scFv.

9. The kit of claim 4, wherein the antibody fragments are any one of a Fab, a F(ab$^2$), a Fv or a scFv.

10. The kit of claim 8, wherein the antibodies that specifically bind to the proteins are single chain antibodies (scFv).

11. The kit of claim 9, wherein the antibodies that specifically bind to the proteins are single chain antibodies (scFv).

12. The kit of claim 2, wherein said antibodies that specifically bind to the proteins are monoclonal antibodies or fragments thereof.

13. The kit of claim 2, wherein said antibodies that specifically bind to the proteins are polyclonal antibodies or fragments thereof.

14. The kit of claim 2, wherein the antibodies that specifically bind to the proteins are labeled.

15. The kit of claim 14, wherein the antibodies are fluorescently-labeled, luminescently-labeled, radioactively-labeled or labeled for ELISA detection.

16. The kit of claim 15, wherein the antibodies are fluorescently labeled.

17. The kit of claim 12, wherein the antibody fragments are any one of a Fab, a F(ab$^2$), a Fv or a scFv.

18. The kit of claim 13, wherein the antibody fragments are any one of a Fab, a F(ab$^2$), a Fv or a scFv.

19. The kit of claim 17, wherein the antibodies that specifically bind to the proteins are single chain antibodies (scFv).

20. The kit of claim 18, wherein the antibodies that specifically bind to the proteins are single chain antibodies (scFv).

* * * * *